United States Patent [19]

Hollevoet

[11] Patent Number: Plant 5,879

[45] Date of Patent: Feb. 10, 1987

[54] DIEFFENBACHIA PLANT (TROPIC SUN)

[75] Inventor: Edmond J. A. Hollevoet, Temse, Belgium

[73] Assignee: L. Gary LeBoss, Homestead, Fla.

[21] Appl. No.: 719,115

[22] Filed: Apr. 2, 1985

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Cushman, Darby & Cushman

[57] ABSTRACT

The plant disclosed, named 'Tropic Sun' is a basal suckering sport of 'Tropic Snow', U.S. Plant Pat. No. 2,869, and is distinguished from 'Tropic Snow' and other known *Dieffenbachia amoena* cultivars by this habit and other characteristics.

1 Drawing Figure

1

My present invention is that of a new and distinct variety of Dieffenbachia plant which I discovered in my greenhouses in Belgium in the course of cultivating the patented variety of *Dieffenbachia amoena* disclosed in U.S Plant Pat. No. 2,869 and commonly known in the United States as *Dieffenbachia amoena* cv. Tropic Snow.

In 1977, in the course of cultivating *Dieffenbachia amoena* cv. Tropic Snow, my attention was drawn to one plant which bore a single solid yellow leaf. This leaf and an adjoining section of cane were removed, and I attempted to establish the leaf coloration by vegetative reproduction. In the course of this endeavor, the solid yellow foliage characteristic was not stable, but cane cuttings were discovered having the unusual characteristic of producing numerous multiple stems at the base of the plant immediately adjacent to the point where roots are produced. Normally, *Dieffenbachia amoena* and its varieties, including the variety Tropic Snow, produce only a single cane or, rarely, two canes, when reproduced by cane or tip cuttings. Mechanical damage to the growing tip often results in one or more branches being produced along a cane, but only rarely results in a new cane being produced at the root base. Because of this unusual charcteristic of producing multiple, basal stems, the plant in question formed a clump of canes, with the number of canes increasing with age. Realizing that this unusual characteristic would be beneficial for ornamental horticultural uses, I immediately began a program of cultivating this sport to establish whether this trait would be retained in successive generations asexually reproduced.

Through continued observation of this sport over seven years and several generations, grown under varying conditions, I have determined that it is a distinct, new variety different from its parent as well as other *Dieffenbachia amoena* varieties of which I am aware.

There are two varieties of Dieffenbachia which have a degree of superficial similarity to my new variety. The first is the parent variety, *Dieffenbachia amoena* cv. Tropic Snow, for which U.S. Plant Pat. No. 2,869 was issued. My new variety is readily distinguishable from *Dieffenbachia amoena* cv. Tropic Snow due to my new variety's charcteristic of naturally and regularly producing multiple stems from the root base, which develop into canes. Like the species *Dieffenbachia amoena,* the cultivar Tropic Snow forms a single cane, with production of a second cane occurring infrequently and usually only after damage to the plant, such as by physical removal of the growing tip. My new variety consistently produces numerous canes in a clumping fashion, without mechanical intervention. Comparing plants of equal maturity grown under the same conditions at Homestead, Fla., *Dieffenbachia amoena* cv. Tropic Snow at 28 inches in height had one cane 2¼ inches in diameter at its broadest point, compared to my new variety having four canes, tallest of which was 26 inches in height, with the three remaining, younger canes being 22 inches, 21 inches and 9 inches in height, and with the four canes having diameters of 2¼ inches, 1¾ inches, 1½ inches and ½ inch. In addition, the foliage coloration differs. Based on measurements taken of leaves of specimens of my new variety and *Diffenbachia amoena* cv. Tropic Snow, grown under the same conditions at Homestead, Fla., with measurements being made of leaves of equal maturity, the central field of white-to-cream coloration covers between 33% and 55% of the otherwise green leaf surface of *Diffenbachia amoena* cv. Tropic Snow, while the central field of white-to-cream coloration covers between 60% and 85% of the otherwise green leaf surface of my new variety. This difference is reflected in measurements of the green margin of the leaves. The green leaf margin of *Dieffenbachia amoena* cv. Tropic Snow is 1 inch to 2¼ inches wide, compared to ½ inch to 1 inch wide for my new variety. Also, the leaf petioles of *Dieffenbachia amoena* cv. Tropic Snow measured between 7 inches and 8 inches, while the leaf petioles of my new variety measured between 5 inches and 6 inches. The result is a plant having leaves of noticeably lighter coloration, which appear broader and smaller. The slightly shorter petioles give my new variety a more compact appearance.

2

The second variety superficially similar to my new variety is a hybrid developed in France at Morel Freres, S.N.C., which is known as Dieffenbachia "Morlof" and which has been, or is being, patented in France. Dieffenbachia "Morlof" is a clumping plant, which forms multiple stems and possesses foliage colored similarly to *Dieffenbachia amoena* cv. Tropic Snow. However, the "Morlof" variety differs from my new variety in that the "Morlof" variety does not produce tall canes, but is a dwarf plant commonly about 12 to 18 inches in height and only rarely exceeding 24 inches in height. In comparison, my new variety grows to heights typical of *Dieffenbachia amoena,* readily reaching a height of 3 to 4 feet, and can be grown to larger heights, if desired, so long as care is exercised to prevent wind damage to the taller canes by staking or like measures. The "Morlof" variety possesses leaf internodes of approximately ¼ inch to 178 inch in length, depending on the maturity of the plant and the cultural conditions in which it is grown. In comparison, the leaf internodes of my variety are ¾ inch to inch long, depending on the maturity of the plant and cultural conditions. The "Morlof" variety is of a densely spreading form, reminiscent of varieties of Aglaonema. In comparison, my variety retains the tall, upright form typical of *Dieffenbachia amoena,* while also possessing the greater lushness which results from the natural production of multiple canes. The foliage of the "Morlof" variety is somewhat more tapered and its leaves are smaller, using the newest fully emerged leaves produced on mature plants for comparison. Based on measurements of specimens grown under similar conditions and of similar maturity, the "Morlof" variety was 14 inches tall, had leaves between 7 inches and 10 inches long and 3½ inches to 5 inches wide, and the white-to-cream central field of the leaves covered between 30% and 50% of the leaf surface. The "Morlof" variety possessed 5 stems of nearly equal height, with diameters of ¾ inches to 1 inch. My new variety was 26 inches tall, had leaves between 16 inches and 17 inches long and 7½ to 8 inches wide, and the white-to-cream central field of the leaves covered between 60% and 85% of the leaf surface. My new variety possessed 4 canes of varying height (ranging from 26 inches to 9 inches, depending on the age of the cane) and varying diameter (ranging from 2¼ inches to ½ inch, depending on the age of the cane).

Thus, my new variety brings to the trade a clumping variety of *Dieffenbachia amoena* possessing beautiful foliage similar to, but more colorful than, the cultivar Tropic Snow and the lush fullness of a multiple cane plant, without the grower having to engage in the artificial practice of potting multiple plants in the same container to produce a similar visual effect.

The accompanying photographic drawing shows a typical specimen plant of my new variety, the color being as nearly true as possible with color illustrations of this type.

The following is a detailed description of my new discovery, based on observations of specimens grown in my greenhouses in Belgium, and also based on experimental growing in Homestead, Fla., since April 1984.

Parentage: Sport of *Dieffenbachia amoena* cv. Tropic Snow (U.S. Plant Pat. No. 2,869).

Propagation: Holds its distinguishing characteristics through succeeding generations by tip and cane cuttings.

Form: Upright clump with multiple canes.

Growth: Vigorous.

Blooming habit: No flowers have been observed on my new variety and no real attempt has been made to induce flowering, since the flowers of *Dieffenbachia amoena* varieties are not considered ornamental.

Foliage:

*Size.*—Varies according to maturity and cultural conditions, with individual leaves in the juvenile stage ranging from 2 inches to 4 inches long and 1 inch to 3 inches wide, with mature plants typically having leaves from 12 inches to 18 inches in length and 6 inches to 9½ inches in width.

*Quantity.*—Each cane produces a quantity of leaves typical of *Dieffenbachia amoena.* Due to the production of multiple canes, however, after one year there usually are approximately three times as many leaves on a plant as are on the typical *Dieffenbachia amoena* grown in the same conditions.

*Color.*—Similar to *Dieffenbachia amoena* cv. Tropic Snow, disclosed in U.S. Plant Pat. No. 2,869, when grown in the same conditions. However, the degree of cream-white variegation in the central area of the leaf extending outward from the solid green mid-rib of the leaf may vary from 60% to 85% of the total leaf surface depending on the growing conditions, with higher light intensity, higher degrees of moisture availability and higher degrees of nutrient availability resulting in a greater portion of the leaf being cream-white. Color descriptions are based upon the Munsell (Limit) Color Cascade published by Macbeth Color and Photometry Division of Kollmorgen Corporation, Baltimore, Md. The dark green margin of the leaves is Munsell (Limit) Color Cascade color 20-15; and the central area is of multiple mottled colors covering the full range of Munsel (Limit) Color Cascade colors 22-1 through 22-5, 24-1 through 24-3, and 23-1 through 23-3, which mottled colors give the appearance of a cream-white center with yellowish highlights.

*Shape.*—Large ovate, with cordate base.

*Texture.*—Smooth on both upper and under sides.

*Margin.*—Slightly undulate.

*Petiole.*—5 inches to 6 inches long, depending on maturity and cultural conditions.

*Internodes.*—¾ inch to 1 inch depending on maturity and cultural conditions. The internode length is about ¾ inch in plants between 2 feet and 3 feet in height, grown in bright light but without direct exposure to sunlight.

*Canes.*—About 1¾ inches to 2¼ inches in diameter when the plant is between 2 feet and 3 feet in height, depending on cultural conditions.

*Disease resistance.*—Same as *Dieffenbachia amoena* when grown under the same conditions.

*Hardiness.*—Tender, unable to withstand freezing temperatures of even a few hours without substantial damage, loses foliage when temperatures drop below 50° to 55° F., and growth is inhibited by temperatures below 60° F.; but able to withstand and flourish in temperatures between 70° to 100° F. if adequate moisture and humidity are provided.

My greenhouse where the new variety was discovered is located in Temse, Belgium. The new variety has been given the name "Tropic Sun".

I claim:

1. A new and distinct variety of Dieffenbachia plant, substantially as herein shown and described, characterized particularly as to novelty by the unique combination of a general similarity to the parent variety, *Dieffenbachia amoena* cv. Tropic Snow, but having the characteristic of producing multiple basal stems which form a clump of canes, while maintaining the upright form and height of the parent, and having a greater degree of variegated foliage coloration and slightly shorter petioles and leaves.

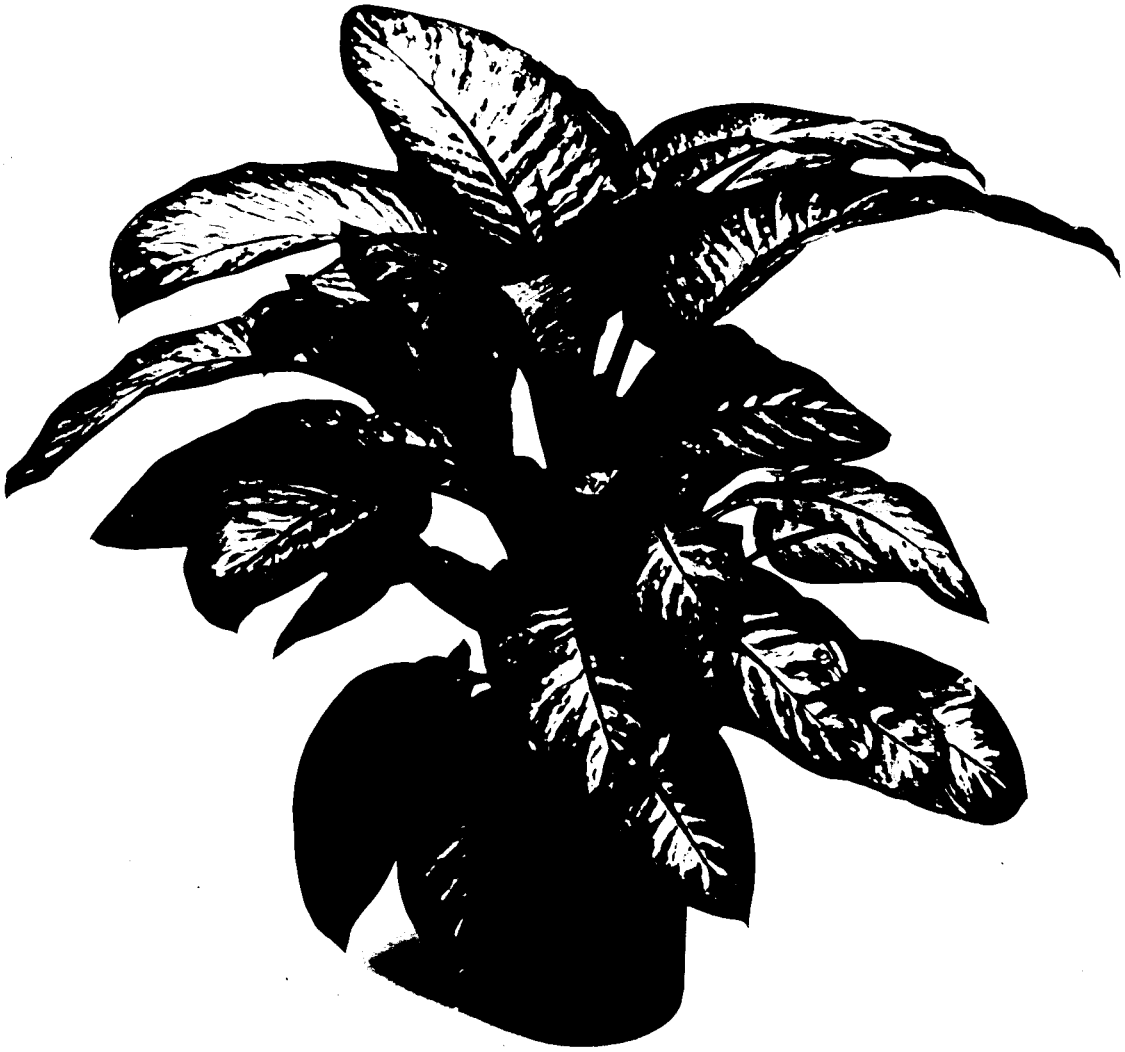

* * * * *